United States Patent
Lavchiev et al.

(10) Patent No.: US 10,345,227 B2
(45) Date of Patent: Jul. 9, 2019

(54) SENSING SYSTEMS AND METHODS USING A COUPLING STRUCTURE

(71) Applicant: Infineon Technologies AG, Neubiberg (DE)

(72) Inventors: Ventsislav Lavchiev, Gallneukirchen (AT); Thomas Grille, Villach (AT); Ursula Hedenig, Villach (AT); Bernhard Jakoby, Linz (AT)

(73) Assignee: Infineon Technologies AG, Neubiberg (DE)

(*) Notice: Subject to any disclaimer, the term of this patent is extended or adjusted under 35 U.S.C. 154(b) by 40 days.

(21) Appl. No.: 15/617,246

(22) Filed: Jun. 8, 2017

(65) Prior Publication Data

US 2017/0268991 A1    Sep. 21, 2017

Related U.S. Application Data (63) Continuation of application No. 14/338,390, filed on Jul. 23, 2014, now Pat. No. 9,702,813.

(51) Int. Cl.
*G01N 21/27* (2006.01)
*G01N 21/77* (2006.01)
*G01N 21/03* (2006.01)

(52) U.S. Cl.
CPC ......... *G01N 21/27* (2013.01); *G01N 21/0303* (2013.01); *G01N 21/7703* (2013.01); *G01N 2021/0382* (2013.01); *G01N 2201/08* (2013.01)

(58) Field of Classification Search
CPC .............. G01N 21/27; G01N 21/0303; G01N 21/7703; G01N 2021/0382; G01N 2201/08

(Continued)

(56) References Cited

U.S. PATENT DOCUMENTS 5,390,021 A    2/1995    Nagata et al.
5,822,472 A *  10/1998   Danielzik ............ G01N 21/648
                                                       385/12

(Continued)

FOREIGN PATENT DOCUMENTS

CN    1885074 A    12/2006
CN    101021593 A   8/2007

(Continued)

OTHER PUBLICATIONS

Mid-infrared rib waveguide absorption sensors based on Si by ventsislav et al, published in proceddings of SPIE May 2013.*

(Continued)

*Primary Examiner* — Ryan A Lepisto
(74) *Attorney, Agent, or Firm* — Eschweiler & Potashnik, LLC (57) ABSTRACT

A sensor system having coupling structures is disclosed. The system includes an input coupling structure, an interaction region, and an output coupling structure. The input coupling structure is configured to receive emitted light at a selected coupling efficiency and may provide filtering of the emitted light for a selected wavelength. The interaction region is coupled to the input coupling structure and configured to interact the light from the input coupling structure with a specimen. The output coupling structure is coupled to the interaction region and configured to provide interacted light from the interaction region to the detector.

20 Claims, 6 Drawing Sheets (58) Field of Classification Search
USPC .................................... 385/12, 15, 31, 37
See application file for complete search history.

(56) References Cited

U.S. PATENT DOCUMENTS

| | | | |
|---|---|---|---|
| 6,078,705 A * | 6/2000 | Neuschafer | G01N 21/6452 385/12 |
| 6,542,682 B2 | 4/2003 | Cotteverte et al. | |
| 6,640,034 B1 | 10/2003 | Charlton et al. | |
| 7,082,235 B2 * | 7/2006 | Gunn, III | B82Y 20/00 385/14 |
| 7,289,221 B2 * | 10/2007 | Wang | G01N 21/45 356/477 |
| 7,306,766 B2 * | 12/2007 | Weisbuch | G01N 21/648 422/82.11 |
| 7,579,609 B2 | 8/2009 | Gorrell et al. | |
| 7,738,097 B2 | 6/2010 | Khetani et al. | |
| 7,928,386 B2 * | 4/2011 | Frey | B82Y 20/00 250/336.2 |
| 8,027,556 B2 | 9/2011 | Tokushima | |
| 8,571,373 B2 | 10/2013 | Wang et al. | |
| 8,649,005 B2 | 2/2014 | Tormod | |
| 8,839,683 B2 | 9/2014 | Sabarinathan et al. | |
| 9,618,693 B2 * | 4/2017 | Lavchiev | G01N 21/7746 |
| 2005/0084213 A1 | 4/2005 | Hamann et al. | |
| 2006/0066867 A1 * | 3/2006 | Beausoleil | B82Y 20/00 356/481 |
| 2007/0036479 A1 | 2/2007 | Beausoleil | |
| 2008/0231857 A1 * | 9/2008 | Depeursinge | A61B 5/14552 356/437 |
| 2010/0226609 A1 | 9/2010 | Tokushima | |
| 2011/0194120 A1 * | 8/2011 | Amaratunga | B82Y 20/00 356/477 |
| 2012/0149126 A1 * | 6/2012 | Wilson | B01F 11/0266 436/175 |
| 2012/0248561 A1 | 10/2012 | Hakko | |
| 2012/0301075 A1 | 11/2012 | Wang et al. | |
| 2013/0005606 A1 * | 1/2013 | Chakravarty | G01N 21/253 506/9 |
| 2013/0157882 A1 | 6/2013 | Quan et al. | |
| 2014/0061677 A1 * | 3/2014 | Jakoby | G01N 21/552 257/80 |
| 2014/0106468 A1 * | 4/2014 | Boersma | B82Y 20/00 436/501 |
| 2014/0175272 A1 * | 6/2014 | Samson | G02F 1/0115 250/269.1 |
| 2014/0176957 A1 * | 6/2014 | Bienstman | G01N 21/45 356/477 |
| 2014/0193839 A1 * | 7/2014 | Cunningham | G01J 3/28 435/7.92 |
| 2014/0196179 A1 * | 7/2014 | Englund | B82Y 35/00 850/1 |
| 2015/0355089 A1 * | 12/2015 | Takase | G01N 21/7703 422/82.11 |
| 2015/0362672 A1 * | 12/2015 | Lavchiev | G01N 21/7746 250/343 |

FOREIGN PATENT DOCUMENTS

| | | |
|---|---|---|
| CN | 101042327 A | 9/2007 |
| CN | 101059433 A | 10/2007 |
| CN | 101126714 A | 2/2008 |
| CN | 101825629 A | 9/2010 |
| CN | 102305774 A | 1/2012 |

OTHER PUBLICATIONS

Wehrspohn, Ralf B. et al. "Application of photonic crystals for gas detection and sensing." 2004 Wiley-VCH Verlag GmbH & Co. KGaA. pp. 238-246.
Notice of Allowance dated Mar. 1, 2017 for U.S. Appl. No. 14/338,390.
Final Office Action dated Jul. 12, 2016 for U.S. Appl. No. 14/338,390.
Non-Final Office Action dated Feb. 26, 2016 for U.S. Appl. No. 14/338,390.

* cited by examiner

SENSING SYSTEMS AND METHODS USING A COUPLING STRUCTURE

CROSS REFERENCE TO RELATED APPLICATIONS

This application is a Continuation of U.S. patent application Ser. No. 14/338,390 filed on Jul. 23, 2014, which is hereby incorporated by reference in its entirety.

BACKGROUND

Sensors are utilized in sensing systems to detect phenomena, properties and features such as light, temperature, motion, and the like. One type of sensor is a fluid (liquid or/and gas) sensor, which is operable to sense fluids. Measurements are performed by the sensor on some certain property of the fluid and these measurements are then used to determine the type of the fluid itself or to determine another property of the fluid.

A common sensor is an absorption sensor used for measuring fluids and a typical configuration is a straight waveguide (WG). The straight waveguide configuration uses a straight ridge (rib) through which light passes. The ridge is in contact with a specimen. An output port of the waveguide provides exiting of the light and the output signal changes when the light in the waveguide interacts with the fluid atop. These variations can be measured and correlated to the fluid.

However, such waveguides are relatively insensitive and require very long lengths in order to sufficiently identify varied liquids. Alternatively to increase the sensitivity, multiple waveguides are generally needed and formed as a mesh. This mesh construction is fragile and, as a result, susceptible to damage. An improved sensor is needed.

DETAILED DESCRIPTION

The present invention will now be described with reference to the attached drawing figures, wherein like reference numerals are used to refer to like elements throughout, and wherein the illustrated structures and devices are not necessarily drawn to scale.

Sensor systems and methods are disclosed below that utilize coupling structures to facilitate coupling efficiency. A sensor generally includes a source of electromagnetic radiation, an interaction volume and a detector. The interaction volume can be in form of a waveguide located between input and output coupling structures, which couple the light in from the source into the waveguide and couple light out from the waveguide to the detector. The sensors utilize light to measure properties of the surrounding environment and are utilized for specimen identification, specimen detection, and the like.

The waveguide constitutes an interaction region where light passes through and interacts with the specimen (the fluid). The light attenuates at least partially according to the conditions and/or specimens proximate the waveguide.

Figure 1:
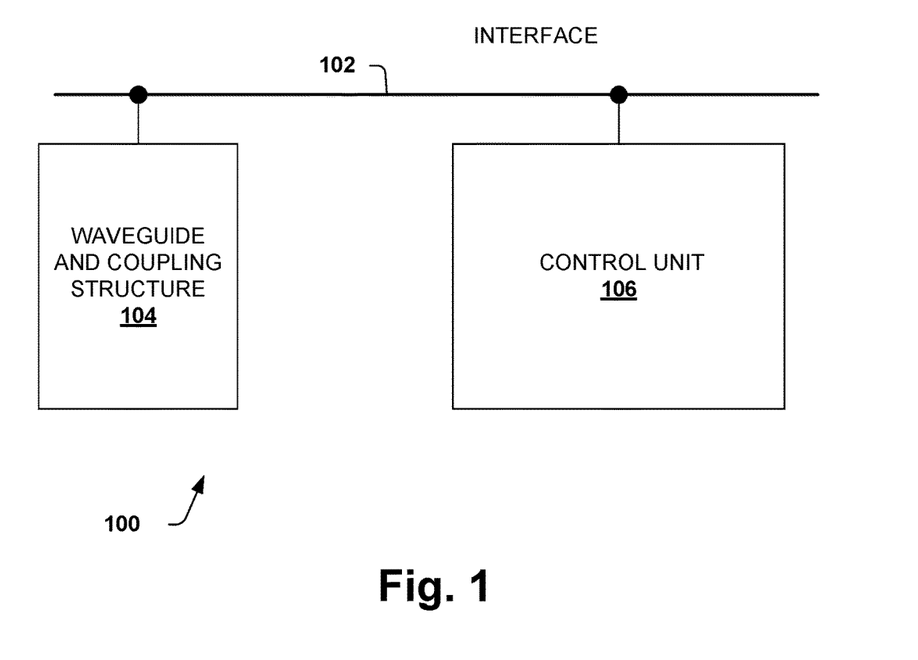
FIG. 1 is a diagram of a sensor system having a coupling structure.

FIG. 1 is a diagram of a sensor system 100 having a coupling structure. The system 100 is provided in a simplified form in order to aid understanding. The system 100 is provided as an example of a system using a waveguide sensor with a coupling structure. The system 100 can be formed or used in one or more devices.

The system 100 includes an interface 102, a sensor 104 and a control unit 106. The interface 102 couples the sensor 104 to the control unit 106. The interface 102 can be configured to provide power and/or signals for communication.

The control unit 106 is configured to control the sensor 104 and to obtain and utilize measurements generated by the sensor 104. For example, the control unit 106 can be configured, in one example, to determine a liquid and a composition of the liquid based on a measurement or output signal from the sensor 104.

The sensor 104 is configured to measure and/or detect specimen(s) proximate the sensor structure 104 with relatively high coupling efficiency. The sensor 104 can be configured to measure chemical and/or environmental properties of a specimen proximate the sensor 104. The specimen can be placed or located in contact with the sensor 104 or in the proximity of 104.

The sensor 104 includes one or more coupling structures configured to mitigate coupling losses and facilitate coupling efficiency. The coupling structures permit light to enter a waveguide from a light source and exit the waveguide for measuring at a detector.

Coupling losses are attenuation and/or loss of light from entering and/or exiting the waveguide via the coupling structures. As shown below, light from a light source necessarily needs to enter and exit the waveguide/interaction region. The coupling structure constitutes either a gratings (corrugation of the surface) or a 2D arrangement of holes in the slab of the waveguide (a 2D PhC). The coupling structures are configured to direct light from the light source into the waveguide and to direct light from the waveguide to the detector. Coupling losses occur due to the grating, the 2D PhC coupler, and the like. The higher the coupling losses, the more light needs to be generated and the higher the sensitivity needed for the detector.

The coupling structures of the sensor 104 are configured to mitigate coupling losses, enhance coupling efficiency and facilitate homogeneity of sensor components by including and configuring tapered portions and other properties. Some of the other properties include composition, materials, lattice structure, corrugation of a surface, and the like.

Additionally, the coupling structures of the sensor 104 are configured to select wavelengths of light and act as a filter. The wavelengths can be selected by (i) the periodicity of the grating, (ii) the periodicity and the radius of the 2D PhC coupler, and (iii) the periodicity and the radius of the 2D PhC WG and the other properties. For example, the coupling structures can be configured to pass only infra-red wavelengths of light.

The light source is directed at an input coupling structure configured to introduce emitted light into the interaction region. The light detector or photo-detector is positioned about an output coupling structure, which is configured to direct exited light toward the detector.

As light passes through an interaction region, the light changes in terms of one or more of its characteristics. In one example, light attenuation occurs. In another example, a shift of the maximum of the light intensity on the spectra scale can occur. The attenuation varies according to a specimen in contact with or proximate to the interaction region. The detector measures the output light. This information or measurement can be provided to the control unit 106 for analysis. The measurement correlates to the specimen and includes, for example, specimen type, liquid, gas, temperature, and the like.

Figure 2A:
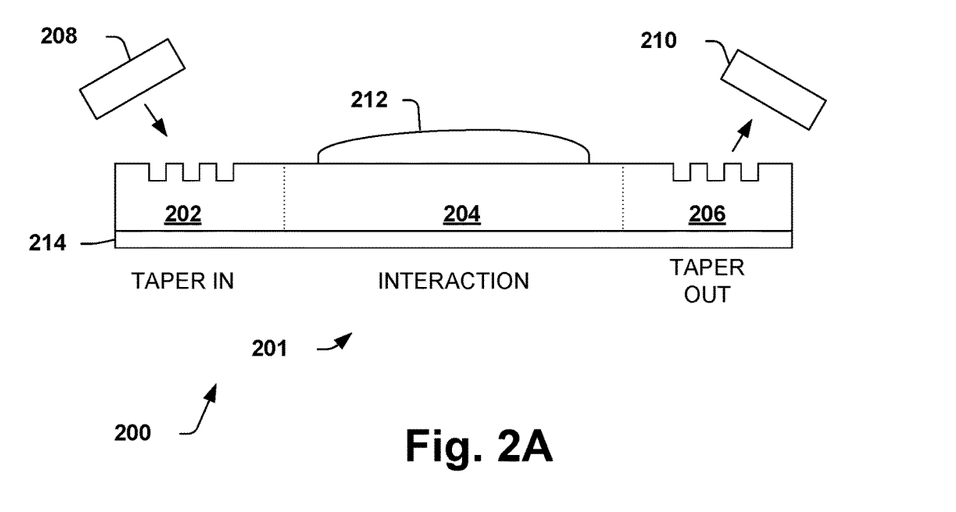
FIG. 2A is a diagram illustrating a side view of one possible configuration of a sensor having a waveguide and coupling structures.
Figure 2B:
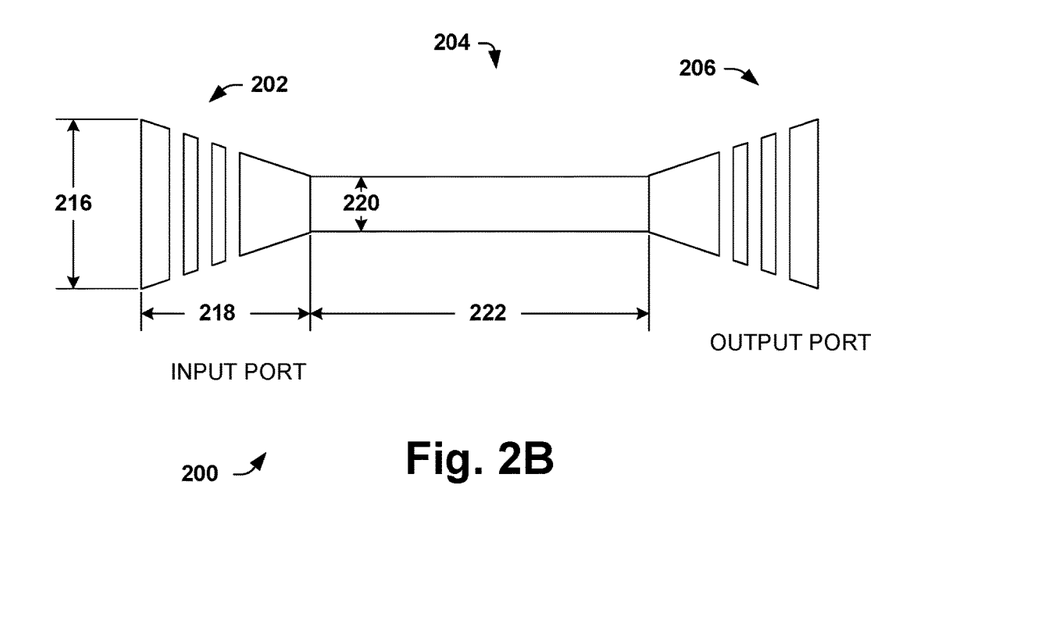
FIG. 2B is a diagram illustrating a top view of the sensor having a coupling structure, a waveguide and a taper

FIGS. 2A and 2B describe a sensor system 200 including a waveguide and coupling structures. The coupling structures are configured to enhance coupling efficiency and provide wavelength selectivity.

FIG. 2A is a diagram illustrating a side view of a sensor system 200 having coupling structures. The sensor system 200 is utilized to detect and/or measure fluid and the like proximate to the sensor 200. The sensor system 200 uses an interaction region 204 where light passes through and is attenuated according to a specimen 212. Characteristical for each fluid is its absorption coefficient, which results in the characteristical attenuation.

The sensor 200 includes an element 201, a light source 208 and a light detector 210. The element 201 includes an input coupling structure 202, a waveguide interaction region 204, and an output coupling structure 206. The light source 208 emits an electromagnetic field (light). The light source 208 can be configured to emit a particular wavelength of light, such as infrared. The detector 210 is configured to detect or measure the wavelength of light emitted by the light source 208 after it passes through the interaction region 204 (the waveguide). A specimen 212 is located proximate to or in contact with the waveguide/interaction region 204. The specimen 212 can include a liquid and/or a gas.

The input coupling structure 202, the interaction region 204 and the output coupling structure 206 are formed on a membrane 214. The coupling structures 202 and 206; and the region 204 are comprised of a suitable material, such as silicon (Si), lead sulfide (PbS), lead selenide (PbSe), silicon nitride ($Si_xN_y$), and have suitable dimensions. In one example, the waveguide region 204 has a width of 2 micrometers and a height of 600 nanometers. Other characteristics can also be selected or adjusted including, but not limited to, shape for the interaction region 204, materials, position of the source and the detector and the like. In one example, the waveguide is or is formed in a photonic crystal or segmented waveguide that has periodic changes in its cross section/refractive index. The photonic crystal or segmented waveguide can be formed with 2D patterning.

Generally, a photonic crystal is a periodic structure of two types: air holes in a material slab and material rods in air. For air holes in a material slab, the air holes are arranged in a periodic lattice. For material rods in air, the rods are arranged in a periodic lattice. An example of a photonic crystal is described below. The holes in the slab can be filled with material having different index of refraction in comparison to the material of the slab.

The input coupling structure 202 receives the emitted light from the light source 208 and directs the light to the interaction region 204. In one example, the light source 208 is positioned off plane with respect to the interaction region 204 (the waveguide) and the input coupling structure 202 is configured with a grating, voids or corrugations to allow the light to enter. In another example, the light source 208 is positioned in the plane of 204 so that to direct the emitted light through the waveguide 201 without the need of couplers. The grating has suitable dimensions, such as a grating period, grating height and length of grating region (e.g., 2 mm), in order to allow sufficient light to enter.

The membrane 214 is comprised of a suitable material for supporting the element 201 and, typically, a number of other waveguides/sensors. Additionally, the suitable material is selected to provide membrane/substrate requirements and characteristics including, for example, index of refraction, flexibility, and the like. The membrane 214 can be somewhat rigid or flexible, depending on the materials used. In one example, the membrane 214 includes a honeycomb structure on its back side with respect to the waveguide, which facilitates strength while permitting flexibility. In one example, the suitable material is Silicon Nitride. In another example, the suitable material has a low refractive index.

The interaction region 204 is configured to cause the guided light to pass or propagate. The size and shape of the region 204 is configured for a selected wavelength(s) and attenuation rate. As the guided light passes through the absorption region, the guided light is attenuated according to the specimen 212. Thus, varied specimen types and characteristics, such as age and temperature, yield different absorption rates through the region. As a result, the guided light exits the interaction region 204 attenuated at a rate dependent at least partially on the specimen. Thus, the interacted light is attenuated when compared with the emitted light or with the light without the specimen 212.

The interacted light exits at the output coupling structure 206. The interacted light is measured by the detector 210. In one example, the output coupling structure 206 has grating to allow the interacted light to exit the waveguide 201.

The detector 210 measures the exiting light from the output coupling structure 206. The exiting light is attenuated compared with the emitted light or with the light without the specimen 212. The detector 210 or another component, such as a controller, uses the measured light to determine a composition and other characteristics of the specimen 212. In one example, the detector 210 is configured to be off plane/line with the waveguide.

The detector 210 can be configured to measure a selected spectral range or selected wavelengths of light, such as infrared. In one example, the waveguide 200 is configured to sense wavelengths of around 5-6 micro-meters.

The input coupling structure 202 is configured with a tapered shape that facilitates entry of light from the light source 208. Generally, the tapered shape permits a beam width of the light source 208 to exceed a width of the interaction region 204. Thus, the tapered shape collects or focuses the beam from the light source to a smaller width.

The input coupling structure 202 comprises either a grating (which is a one dimensional corrugation of the surface) or a two dimensional corrugation of the surface (2D PhC). The PhC has a selected lattice structure, periodicity and dimensioning. The surface configuration of the coupling structure 202 assists in improving homogeneity of the sensor 200.

The output coupling structure 206 is also configured with a tapered shape that facilitates exiting of the interacted light.

Generally, the tapered shape permits use of a detector wider than a beam width of the light within the interaction region 204. Thus, the exiting light has a width that exceeds the width within the interaction region 204. The tapered shape also improves the homogeneity, which further improves the performance of the sensor by reducing the amount of light coupling losses into and out of the waveguide.

The output coupling structure 206 comprises either a grating (which is a one dimensional corrugation of the surface) or a two dimensional corrugation of the surface (2D PhC). The PhC has a selected lattice structure, periodicity and dimensioning. Additionally, the surface configuration assists in improving homogeneity of the sensor 200. The homogeneity improves further the performance of the sensor by reducing the amount of light coupling losses into and out of the waveguide.

FIG. 2B is a diagram illustrating a top view of the sensor system 200 having a waveguide and coupling structures. The sensor 200 is utilized to detect and/or measure fluid and the like proximate to the sensor 200. The sensor 200 of FIG. A is shown in FIG. 2B with the top view in order to illustrate the tapered shape of the coupling regions.

The sensor 200 is depicted with the input coupling structure 202, the interaction region 204 and the output coupling structure 206. The coupling structures 202 and 206 are illustrated with the tapered shape and gratings for entry and exit of light.

The input coupling structure 202 has a larger width 216 at an entry side and a narrower width 220 at an exit side. The structure 202 also has a length 218. The exit width 220 is typically the width of the interaction region 204 and accommodates a light beam width at or below that width. The entry width 216 is configured to match the emitted light of the light source 208. A profile exists between the entry side and the exit side of the structure 202. In this example, the profile is shown as a straight line. However, other profiles can be used, such as a curved profile and the like.

The output coupling structure 206 has a larger width 216 at an exit side and a narrower width 220 at an entry side. The structure 206 also has a length 218, which is the same as the length of the input coupling structure 202 in this example. The entry width 220 is typically the width of the interaction region 204 and accommodates a light beam width at or below that width. The exit width 216 is wider than the entry width and is selected to accommodate the detector 210. A profile exists between the entry side and the exit side of the structure 202. In this example, the profile is shown as a straight line. However, other profiles can be used, such as a curved profile and the like.

The dimensions and profile for the structures 202 and 206 are shown as being identical in FIG. 2B. However, it is appreciated that the structures 202 and 206 can have dimensions and profiles that vary from each other.

Figure 3A:
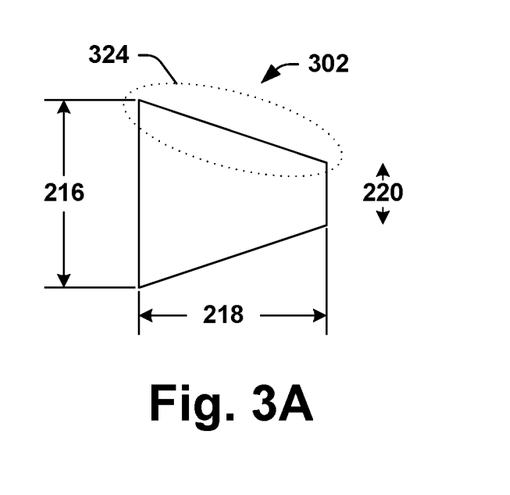
FIG. 3A is a diagram showing an example taper profile for a coupling structure.

FIG. 3A is a diagram showing an example taper profile for a coupling structure 302. The structure can be configured for use as an input coupling structure and/or an output coupling structure.

The coupling structure 302 is shown with a first side width 216, a second side width 220 and a length 218. The structure 302 has a taper profile 324 from the first side to the second side. In this example, the taper profile is a straight line.

Figure 3B:
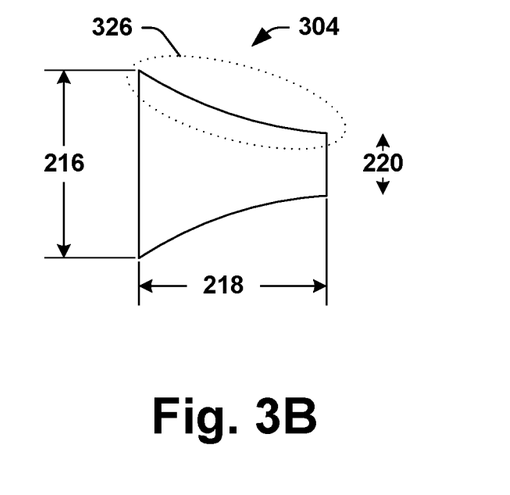
FIG. 3B is a diagram showing an example curved taper profile for a coupling structure.

FIG. 3B is a diagram showing an example curved taper profile for a coupling structure 304. The structure can be configured for use as an input coupling structure and/or an output coupling structure.

The coupling structure 304 is shown with a first side width 216, a second side width 220 and a length 218. The structure 304 has a taper profile 326 from the first side to the second side. In this example, the taper profile is a curve.

Generally, the taper profile is configured to accommodate the beam width and transition the beam from one side to the other while mitigating coupling loss. Additionally, the taper profile is configured for efficient transition of the light to/from the coupling structure and the interaction region. Further, the taper profile can be configured to filter or accommodate selected wavelengths.

The taper profiles, for example, can be linear, based on experimentation, based on a squares function, and the like.

Figure 4:
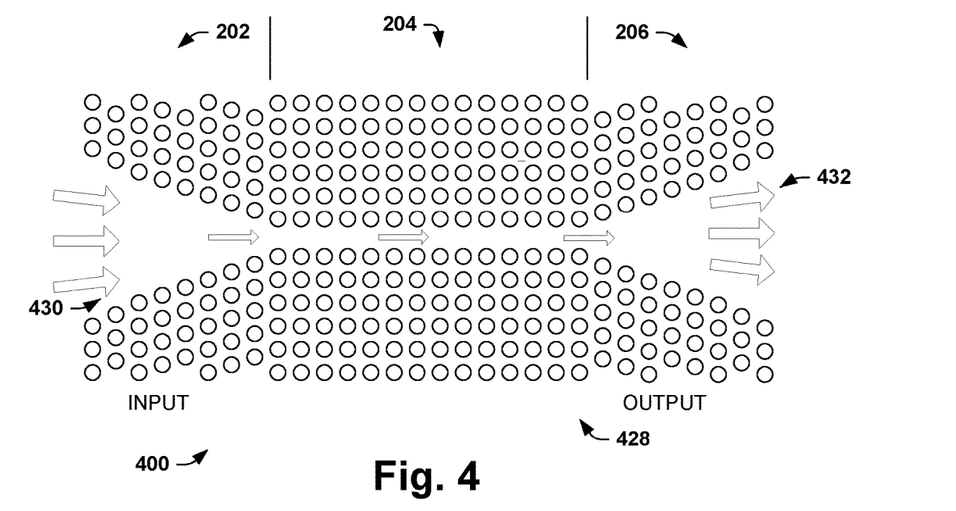
FIG. 4 is a diagram illustrating a photonic crystal (PhC) based waveguide with no pattern in the coupling regions.

FIG. 4 is a diagram illustrating a photonic crystal based sensor element 400. The element 400 can be used for the sensor 104, described above.

The element 400 includes an input coupler structure 202, an interaction region 204 and an output coupler structure 206. The element 400 is formed with a photonic crystal and has characteristics selected to mitigate coupling losses, enhance coupling efficiency and to filter emitted light. Generally, the element 400 is configured to have the selected characteristics including material, composition, periodicity, lattice structure, pattern, void/hole diameter, profile and the like. The element 400 has a photonic band gap (PBG), which permits only wavelengths within the photonic band gap to propagate along the element 400.

Light or electromagnetic radiation is shown as arrows and enters the input coupling region 202, interacts in the interaction region 204 and exits via the output coupling region 206.

The periodicity is a distance from a center of a hole/void to a center of adjacent holes/voids. Thus, a smaller periodicity results in a greater density of voids. The lattice structure is an arrangement of the voids. FIG. 4 shows a square or rectangular arrangement of voids. Other lattice structures are contemplated including, for example, hexagonal, hexagonal rings and the like.

The element 400 is formed by forming a slab of photonic crystal based material on a membrane, such as the membrane 214 described above or just a solid substrate. The slab is comprised of a suitable material, such as a silicon based material. Holes or voids are formed within the slab and are shown as circles in FIG. 4. The voids can be filled in with a fill material, such as SiOx, SiN, and the like or have no fill material.

The input coupling structure 202 is configured to have selected characteristics to efficiently receive light from a light source and filter wavelengths so only selected wavelengths enter the interaction region 204. The selected characteristics include material, composition, periodicity, lattice structure, pattern, void/hole diameter, profile and the like. A surface of the structure 202 can be corrugated to facilitate entry of light. In FIG. 4, the input coupling structure 202 is shown with no patterning 430.

The output coupling structure 206 is also configured to have selected characteristics to efficiently provide interacted light from the interaction region 204 to a detector and filter wavelengths so only selected wavelengths exit the output coupling structure 206. The selected characteristics include material, composition, periodicity, lattice structure, pattern, void/hole diameter, profile and the like. A surface of the structure 206 can be corrugated to facilitate exit of light. In FIG. 4, the output coupling structure 206 is shown with no patterning or voids 432.

The interaction region/waveguide 204 is configured to have selected geometrical characteristics in order to allow specific wavelengths to propagate (i.e. to have the specific photonic band gap) from the input coupling structure 202.

The propagating light interacts and is attenuated at least partially according to a specimen proximate the region 204. In this example, the interaction region 204 omits voids, however it is appreciated that other suitable configurations are contemplated.

Figure 5:
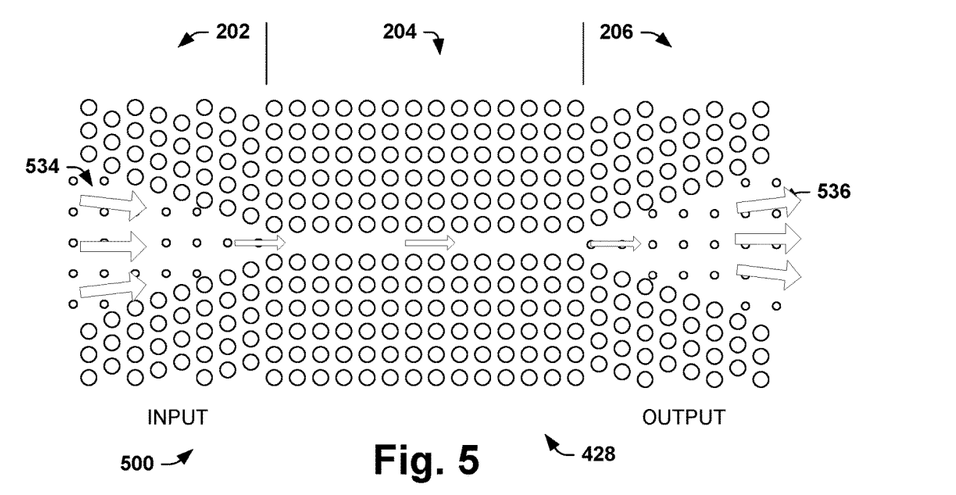
FIG. 5 is a diagram illustrating a photonic crystal based waveguide with a coupling pattern in a form of a two dimensional (2D) photonic crystal in the coupling regions.

FIG. 5 is a diagram illustrating a photonic crystal based element 500. The element 500 can be used for the sensor 104, described above.

The element 500 includes an input coupler structure 202, an interaction region 204 and an output coupler structure 206. The waveguide 500 is formed with a photonic crystal and has characteristics selected to mitigate coupling losses, enhance coupling efficiency and to filter emitted light. Generally, the element 500 is configured to have the selected characteristics including material, composition, periodicity, lattice structure, pattern, void/hole diameter, profile and the like. The waveguide 500 has a photonic band gap (PBG), which permits only wavelengths within the photonic band gap to propagate along the waveguide 500. In one example, the voids have a circular shape, however the voids can have other shapes, such as a square.

Light or electromagnetic radiation is shown as arrows and enters the input coupling region 202, propagates in the interaction region 204, where it interacts with the specimen and exits via the output coupling region 206.

The element 500 is formed, in one example, by forming a slab of photonic crystal based material on a membrane, such as the membrane 214 described above. The slab is comprised of a suitable material, such as a silicon based material. Holes or voids are formed within the slab and are shown as circles in FIG. 5. The voids can be filled in with a fill material, such as SiOx, SiN, and the like or have no fill material.

The input coupler structure 202 is configured to have selected characteristics to efficiently receive light from a light source and filter wavelengths so only selected wavelengths enter the interaction region 204. The selected characteristics include material, composition, periodicity, lattice structure, pattern, void/hole diameter, profile and the like. A surface of the structure 202 can be corrugated to facilitate entry of light. In FIG. 5, the input coupling structure 202 is shown with patterning 534. The input patterning 534 has a different periodicity and voids diameter from that of the surrounding portions of the waveguide 500. The geometrical characteristics of the pattern 534 are selected so that to fill the phase matching condition required for coupling of light in and out of the waveguide.

The output coupler structure 206 is also configured to have selected characteristics to efficiently couple out light from the interaction region 204 to a detector. The selected characteristics include material, composition, periodicity, lattice structure, pattern, void/hole diameter, profile and the like. A surface of the structure 206 can be corrugated (instead of the 2D PhC structure) to facilitate exit of light. In FIG. 5, the output coupling structure 206 is shown with patterning 536. The output patterning 536 has a different periodicity and voids diameter than that of the surrounding portions of the waveguide 500.

The interaction region 204 is configured to have selected characteristics to interact with emitted light from the input coupling structure 202. The emitted light interacts and is attenuated at least partially according to a specimen proximate the region 204. In this example, the interaction region 204 again omits voids or holes, however it is appreciated that other suitable configurations are contemplated.

Figure 6:
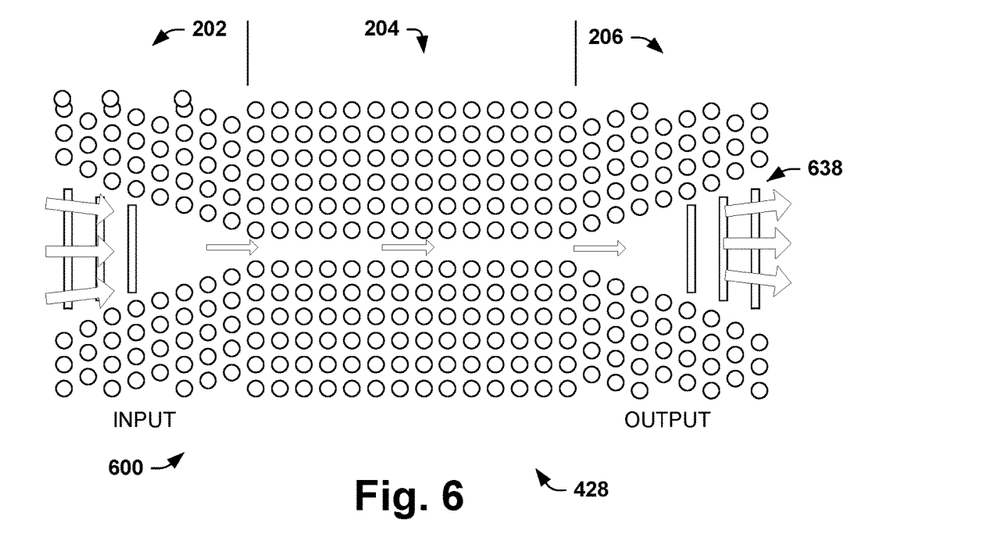
FIG. 6 is a diagram illustrating a photonic crystal based waveguide with a grating pattern as a coupler.

FIG. 6 is a diagram illustrating a photonic crystal based element 600. The element 600 can be used for the sensor 104, described above.

The element 600 includes an input coupler structure 202, an interaction region 204 and an output coupler structure 206. The element 600 is formed with a photonic crystal and has characteristics selected to mitigate coupling losses, enhance coupling efficiency and to filter emitted light. Generally, the element 600 is configured to have the selected characteristics including material, composition, periodicity, lattice structure, pattern, void/hole diameter, profile and the like. The element 600 has a photonic band gap (PBG), which permits only wavelengths within the photonic band gap to propagate along the waveguide 600.

Light or electromagnetic radiation is shown as arrows and enters the input coupling region 202, interacts in the interaction region 204 and exits via the output coupling region 206.

The element 600 is formed by forming a slab of photonic crystal a membrane, such as the membrane 214 described above. The slab is comprised of a suitable material, such as a silicon based material. Holes or voids are formed within the slab and are shown as circles in FIG. 6. The voids can be filled in with a fill material, such as SiOx, SiN, and the like or have no fill material.

The input coupling structure 202 is configured to have selected characteristics to efficiently receive light from a light source and filter wavelengths so only selected wavelengths enter the interaction region 204. The selected characteristics include material, composition, periodicity, lattice structure, pattern, void/hole diameter, profile and the like. A surface of the structure 202 can be corrugated to facilitate entry of light. In FIG. 6, the input coupling structure 202 is shown with two dimensional grating 638.

The output coupling structure 206 is also configured to have selected characteristics to efficiently provide interacted light from the interaction region 204 to a detector and filter wavelengths so only selected wavelengths exit the output coupling structure 206. The selected characteristics include material, composition, periodicity, lattice structure, pattern, void/hole diameter, profile and the like. A surface of the structure 206 is corrugated to facilitate exit of light. In FIG. 6, the output coupling structure 206 is shown with two dimensional grating 638.

The interaction region 204 is configured to have selected characteristics to interact with the light from the input coupling structure 202. The propagating light interacts and is attenuated at least partially according to a specimen proximate the region 204. In this example, the interaction region 204 again omits voids or holes, however it is appreciated that other suitable configurations are contemplated.

FIGS. 4-6 depict examples of patterns for illustrative purposes and to facilitate understanding. It is appreciated that other suitable configurations can be utilized for the coupling structures and waveguides, including combinations of the above.

Figure 7:
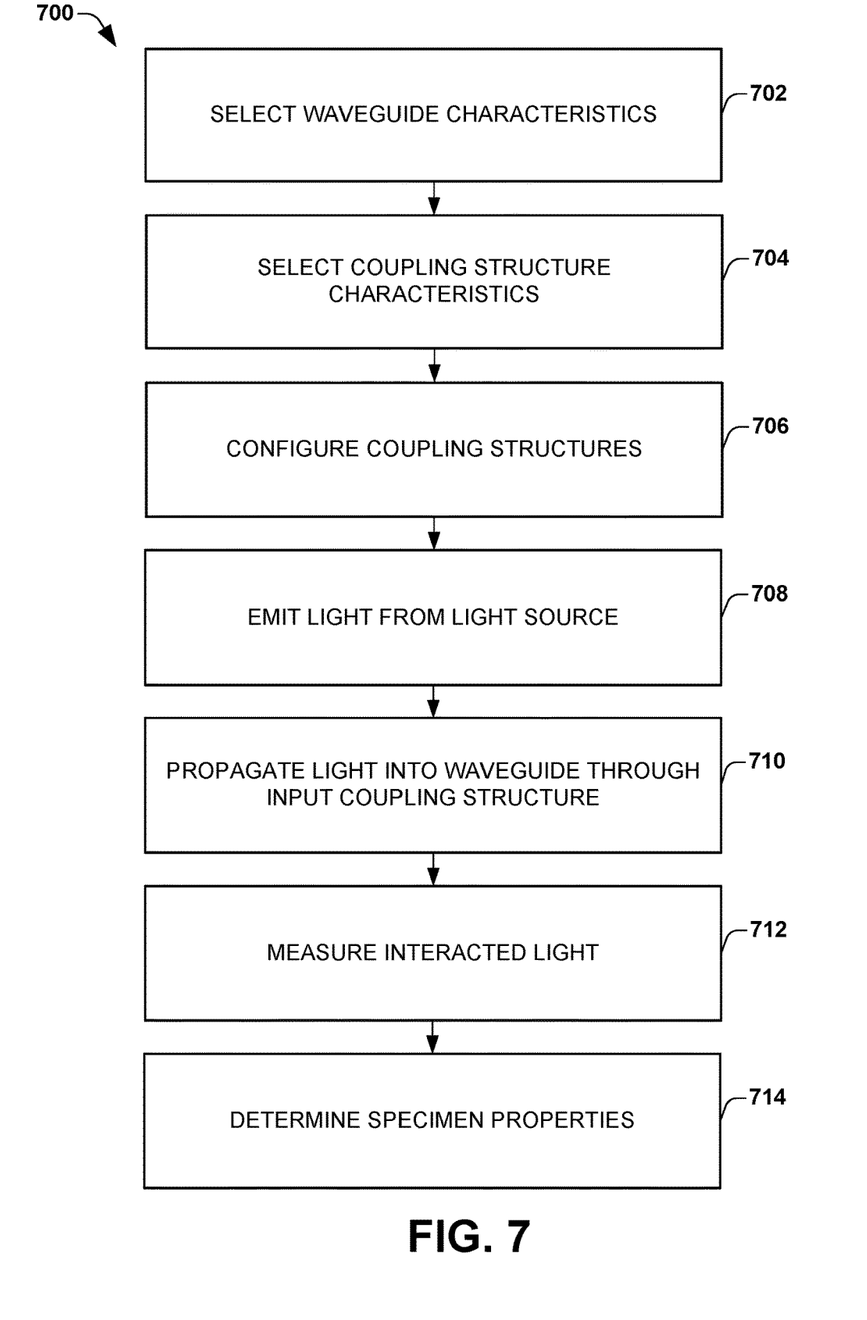
FIG. 7 is a flow diagram illustrating a method of operating a sensor having coupling structures.

FIG. 7 is a flow diagram illustrating a method 700 of operating a sensor having coupling structures. The coupling structures are configured to couple/propagate light from the light source to the waveguide and from the waveguide to the detector, enhance coupling efficiency and provide wavelength selectivity.

The method 700 begins at block 702, where waveguide characteristics including, a wavelength or range of wavelengths and a coupling efficiency, are selected. The wavelength can be selected according to a specimen and/or types of specimens to be detected. Additionally, the wavelength can be selected to detect particular chemical properties and environmental properties. In one example, the wavelength is selected to only include infra-red light. The coupling efficiency is selected according to a light source and/or detector. For example, a higher efficiency allows a lower powered light source and a lower sensitivity detector. A control unit, such as the control unit 106 described above, can be configured to select the wavelengths.

The other waveguide characteristics include internal or interaction region beam size, light source beam size, detector beam size, absorption rates, and the like.

Coupling structure characteristics are selected at block 704 at least partially according to the waveguide characteristics, including the selected wavelength and the selected coupling efficiency. The characteristics include periodicity, hole diameter, dimensions, materials, lattice structure and the like. For example, an entry side for an input coupling structure is configured to have a width dimension that accommodates a beams size of emitted light from the light source. Some examples of structure characteristics are described in additional detail above. The control unit 106 can be configured to select the structure characteristics.

Coupling structures are configured at block 706 according to the coupling structure characteristics. This includes, for example forming a slab on a membrane and configuring the slab with voids at selected diameters, periodicity and lattice structure. An interaction region is also configured, thus a waveguide including an input coupling structure, an interaction region and an output coupling structure is configured.

A light source emits light having the selected wavelength at block 708. The light source, in one example, is controlled to provide only the selected wavelength. In another example, the light source is configured to provide a range of wavelengths including the selected wavelength(s).

The emitted light passes through the interaction region at block 710. As the light propagates into the input coupling structure and through the interaction region, portions of the light are absorbed by a specimen proximate to the interaction region. The absorption rate depends at least partially on the specimen.

The interacted light exits the waveguide through the output coupling structure and is measured by a detector at block 712. The light detector captures and measures the light that has interacted and exited the waveguide.

Specimen properties are determined according to the emitted light and the measured light at block 714. The properties include chemical and/or environmental properties. Additionally, the specimen type can be determined at block 714. The light detector and/or a separate controller can be configured to make the determination.

While the method is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the disclosure herein. Also, one or more of the acts depicted herein may be carried out in one or more separate acts and/or phases.

It is appreciated that the claimed subject matter may be implemented as a method, apparatus, or article of manufacture using standard programming and/or engineering techniques to produce software, firmware, hardware, or any combination thereof to control a computer to implement the disclosed subject matter (e.g., the systems shown in FIGS. 1, 2, etc., are non-limiting examples of system that may be used to implement the above methods). The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

A sensor system having coupling structures is disclosed. The system includes an input coupling structure, an interaction region, and an output coupling structure. The input coupling structure is configured to receive emitted light at a selected coupling efficiency and to filter the emitted light for a selected wavelength. The interaction region is coupled to the input coupling structure and configured to propagate the light and to allow interaction of the propagating light with the specimen. The output coupling structure is coupled to the interaction region and configured to provide interacted light from the interaction region.

Another sensor system having coupling structures is disclosed. The system includes a sensor and a control unit. The sensor has a light source, a waveguide and a detector. The light source is configured to emit light that includes a selected wavelength, such as infra-red. The waveguide has an input coupling structure, an interaction region, and an output coupling structure. The input coupling structure is configured to receive the emitted light, but may also filter the emitted light according to the selected wavelength. The interaction region is configured to absorb a portion of the light according to a specimen. The output coupling structure is configured to provide interacted light. The detector is configured to measure the interacted light from the waveguide. The control unit is coupled to the sensor and is configured to determine properties of the specimen according to the measured light and the emitted light.

A method of operating a sensor having coupling structures is disclosed. Waveguide characteristics, including a wavelength and coupling efficiency, are selected. Coupling characteristics are selected according to the waveguide characteristics. An input coupling structure and an output coupling structure are configured according to the selected coupling characteristics.

In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "including", "includes", "having", "has", "with", or variants thereof are used in either the detailed description and the claims, such terms are intended to be inclusive in a manner similar to the term "comprising".

What is claimed is:

1. A sensor having one or more coupling structures, the sensor comprising:
    an input coupling structure having coupling properties and configured to receive emitted light and to focus the received light to a smaller width, the input coupling structure further configured to filter the emitted light; and an interaction region coupled to the input coupling structure to receive the focused and filtered light and to interact the focused and filtered light with a specimen, wherein the received light is wider than a beam width of light in the interaction region.

2. The sensor of claim 1, wherein the coupling properties include a tapered portion.

3. The sensor of claim 1, wherein the coupling properties include one or more of composition, lattice structure, and surface corrugation.

4. The sensor of claim 1, wherein the coupling structure and the interaction region are arranged within a single piece of material.

5. The sensor of claim 4, wherein the coupling structure and the interaction region are provided on a same membrane.

6. The sensor of claim 1, wherein the input coupling structure includes a grating.

7. The sensor of claim 6, wherein the grating is configured to allow the emitted light based on a grating period, grating height and grating length.

8. The sensor of claim 1, wherein the input coupling structure has an entry width configured to match the emitted light.

9. The sensor of claim 1, wherein the input coupling structure has a tapered profile from an entry side to an exit side.

10. The sensor of claim 9, wherein the tapered profile is curved.

11. The sensor of claim 1, further comprising an output coupling structure coupled to the interaction region and configured to provide interacted light from the interaction region.

12. The sensor of claim 1, further comprising a control unit configured to determine a composition of the specimen based on the interacted light from the interaction region.

13. An optical sensor system having coupling structures, the system comprising:

an input coupling structure, the input coupling structure comprising a tapered photonic crystal structure to focus received light to a smaller width, the input coupling structure further comprising a grating structure within the tapered photonic crystal structure;

an interaction region coupled to the input coupling structure to receive the focused and filtered light, the interaction region configured to interact the emitted light from the input coupling structure with a specimen; and an output coupling structure coupled to the interaction region and configured to provide interacted light from the interaction region to an optical detector.

14. The sensor system of claim 13, wherein the grating structure has a periodicity based on a selected wavelength.

15. The sensor system of claim 13, wherein the output coupling structure has a two dimensional corrugation of its surface.

16. The sensor system of claim 13, wherein the tapered photonic crystal structure has an entry side width that accommodates the received light.

17. A sensor system having coupling structures, the system comprising:

a sensor comprising:
  a light source configured to emit light including a selected wavelength;
  a waveguide comprising:
    an input coupling structure having coupling properties and configured to receive emitted light, wherein the coupling properties are configured according to a selected coupling efficiency;
    an interaction region configured to interact with the emitted light from the input coupling structure and generate interacted light, wherein the received emitted light is wider than a beam width of light in the interaction region; and
    an output coupling structure configured to provide the interacted light from the interaction region; and
  a detector configured to measure the interacted light from the waveguide and generate a measurement based on the interacted light; and
a control unit coupled to the sensor and configured to determine specimen properties based on the measurement from the detector.

18. The system of claim 17, wherein the output coupling structure is configured to provide the interacted light with a beam width greater than a width of the interaction region.

19. The system of claim 17, wherein the input coupling structure has a tapered profile.

20. The system of claim 17, wherein the coupling properties include one or more of composition, lattice structure, and surface corrugation.

* * * * *